United States Patent

Tschirren

[11] Patent Number: 5,824,107
[45] Date of Patent: Oct. 20, 1998

[54] PROSTHETIC JOINT CUP AND INSERT THEREFOR

[76] Inventor: Ernst Tschirren, Steinhübeliweg 9, 3074 Muri b. Berne, Switzerland

[21] Appl. No.: 440,131

[22] Filed: May 12, 1995

[51] Int. Cl.[6] .................................................. A61F 2/34
[52] U.S. Cl. .............................................. 623/22
[58] Field of Search ............................ 623/16, 18, 19, 623/22, 23

[56] References Cited

U.S. PATENT DOCUMENTS 4,936,863   6/1990   Hofmann .
5,376,122   12/1994   Pappas et al. ............................ 623/22

FOREIGN PATENT DOCUMENTS

0483023A1   4/1992   European Pat. Off. .
0552949A1   7/1993   European Pat. Off. .
A2416004    8/1979   France .
A2649005    1/1991   France .
A2653659    5/1991   France .
A1126961    9/1968   United Kingdom .

*Primary Examiner*—David Isabella
*Attorney, Agent, or Firm*—Jacobson, Price, Holman & Stern, PLLC

[57] ABSTRACT

The cup (2) made of a titanium-aluminum alloy is set into the acetabulum. It is thicker on one side (7) than on the opposite side (8). An aperture (17) extends from a center opening (5) of the cup to the rim (20) thereof. At the point of transition of the edges (18, 19) of the aperture to the rim, there are niches (21, 22) for the placement of pincers. This makes it possible to remove a defective insert (11) without damaging the cup or the bone. The cup is provided at its bottom rim with an encircling flange (9) intended to fit into a matching groove (10) of the insert. The cup and the insert come in contact only in this area, thus ensuring optimum introduction of force from the ball head (13) via the insert into the cup.

12 Claims, 5 Drawing Sheets

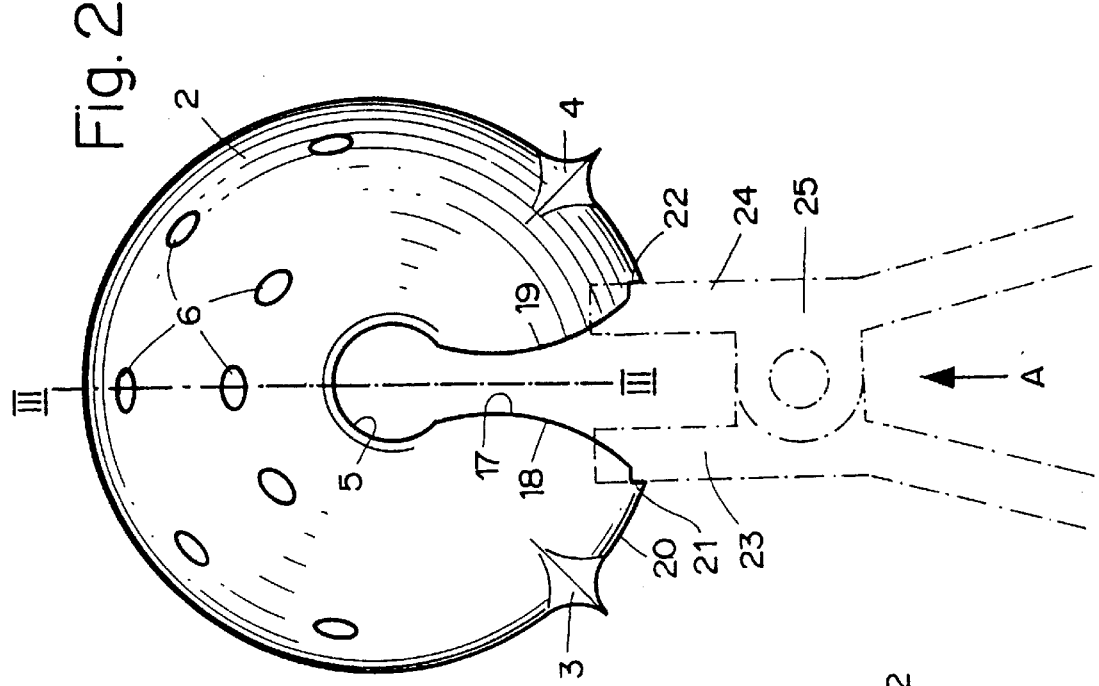
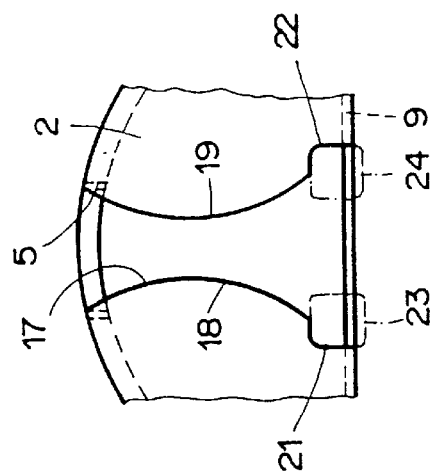
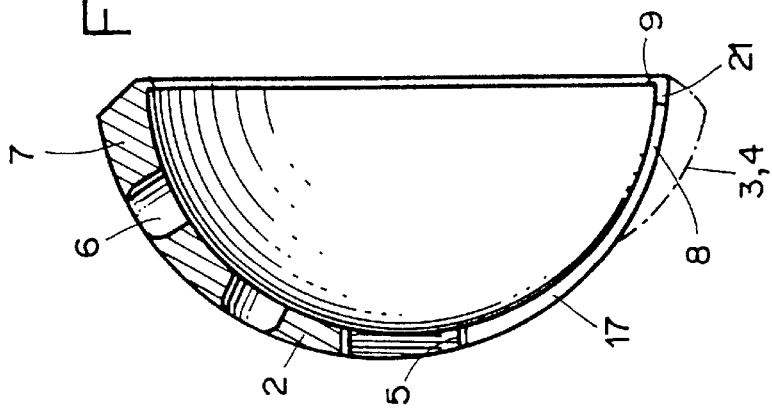

PROSTHETIC JOINT CUP AND INSERT THEREFOR

BACKGROUND OF THE INVENTION

This invention relates to prosthetic devices, and more particularly to a cup for a hip joint prosthesis, as well as to an insert for use with such a cup. The two elements, when joined, form the artificial socket. The invention further relates to a prosthetic joint having a cup and insert as aforesaid.

In the past, polyethylene cups have been cemented into the acetabulum as part of hip joint prostheses. Over the years, if damage occurs, the cup has to be removed, leading to the loss of bone substance during the replacement. A further drawback has been the great amount of wear on the polyethylene.

Another possibility has been to drive ring screws into the acetabulum for insertion of the socket, but such screws eventually loosen. The use of ceramic ring screws had the advantage of eliminating polyethylene attrition.

SUMMARY OF THE INVENTION

It is an object of this invention to provide an improved cup and cup insert, intended to form a socket for a prosthetic joint, especially an artificial hip joint, which do not have the shortcomings of the prior art.

A further object of this invention is to provide a cup and cup insert which ensures optimum introduction of force from the insert loaded by the ball head into the cup.

An additional object is to provide a cup and cup insert in which a certain spring action occurs which absorbs the micromovements of the pelvis and impacts and which is easy on the ceramic insert.

To this end, in the cup according to the present invention, especially for a hip joint prosthesis, an opening extending from the interior to the rim of the cup has side edges which are each provided with at least one niche for the placement of pincers, and the rim of the cup is provided with at least one at least partially encircling first part for engagement with an insert.

The insert according to the present invention, for use with the foregoing cup, is provided adjacent to its edge surface with at least a second at least partially encircling part for engagement with the cup.

In the prosthetic joint according to the present invention, the first encircling part of the cup engages the second encircling part of the insert, the cup and the insert coming in contact only in the region of the first and second encircling parts.

BRIEF DESCRIPTION OF THE DRAWINGS

Preferred embodiments of the invention will now be described in detail with reference to the accompanying drawings, in which:

FIG. 2 is a top plan view of the cup of FIG. 1, FIG. 3 is a cross-section taken on the line III—III of FIG. 2, FIG. 4 is a partial elevation of the cup viewed in the direction of arrow A of FIG. 2.

DESCRIPTION OF THE PREFERRED EMBODIMENTS

Figure 1:
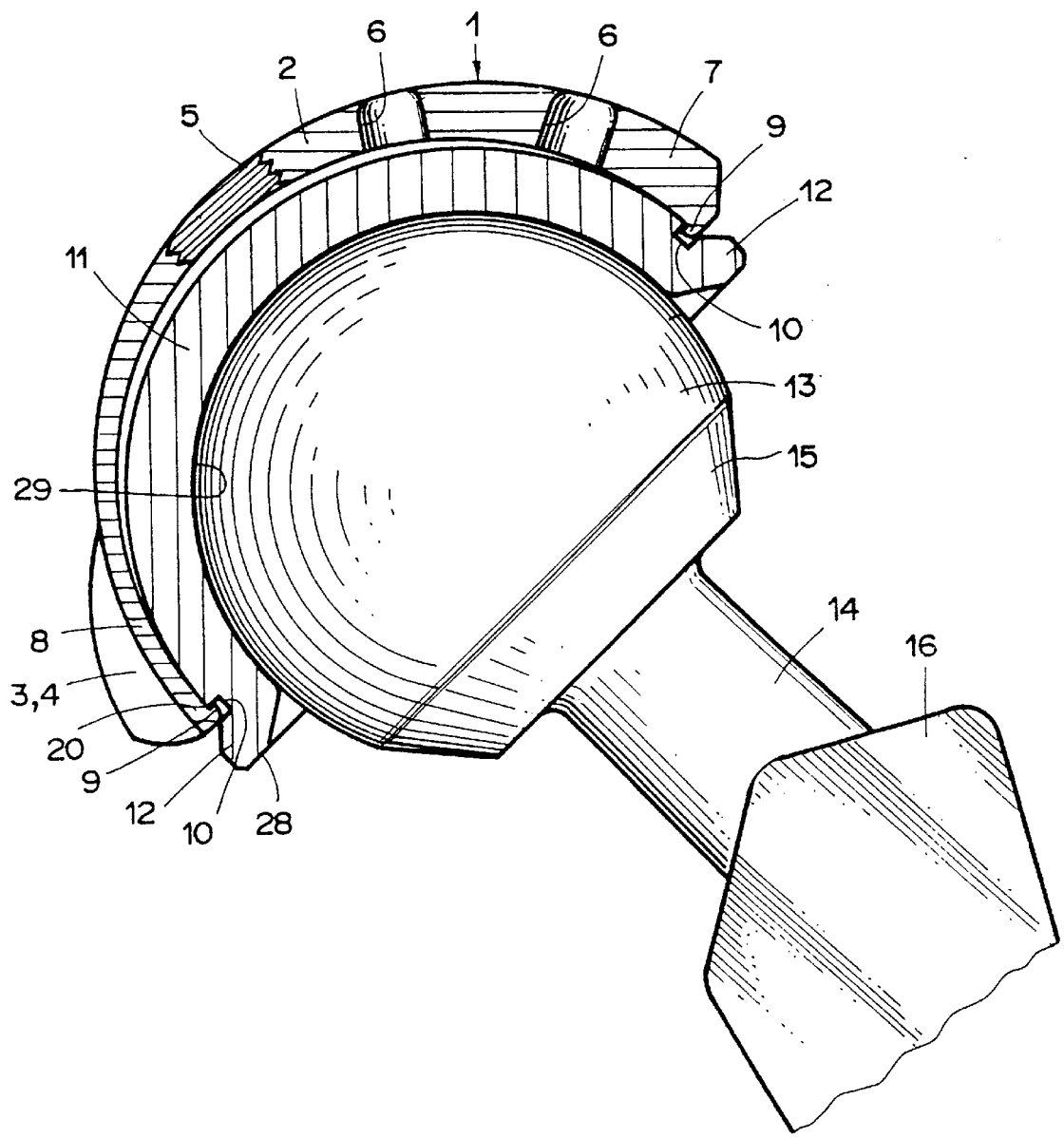
FIG. 1 is a perspective view of a femoral joint prosthesis in a first embodiment of the invention with a cup, an insert, and a ball head, the cup and insert being shown in cross-section.

The hip joint prosthesis illustrated in FIG. 1 is intended to be used when the acetabular socket is damaged. A metal cup 2 formed as a hollow, part-spherical element, say, in the shape of a hollow hemisphere of non-uniform thickness made of a titanium-aluminum allow, preferably $TA_6V_4$, is inserted in the acetabulum (not shown in FIG. 1), fins 3, 4 being pressed into the bone. Cup 2 is self-tightening in the hip socket. An instrument (not shown) having an external thread is screwed into an internally-threaded bore 5 of cup 2, the latter being pressed into the acetabulum by means of this instrument. Cup 2 is further provided with holes 6 through which screws may be driven into the hip bone, if necessary. Cup 2 is thicker on one side, designated by reference numeral 7, than on the other, designated as 8. A spring action and better introduction of force are thereby achieved. The rim of cup 2 is provided with an inwardly projecting, annular flange 9 which engages a matching annular groove 10 in an insert 11. Groove 10 might be in cup 2 and flange 9 on insert 11 instead. Groove 10 and flange 9 might also be designed in several parts, running annularly and separated by gaps. Insert 11, made of aluminum oxide ceramics, is substantially in the shape of a hollow hemisphere and is provided at the rim with an annular shoulder 12 having an edge face 28. A femoral ball head 13, also made of aluminum oxide ceramics, is provided with a chamfer 15 in the region where the neck 14 of a femoral stem 16 is inserted in head 13. Neck 14 and stem 16 are preferably likewise made of the above-mentioned titanium alloy. Insert 11 is ground, at least on its inside surface 29.

In FIG. 2, a top plan view of cup 2, it is seen that leading from the substantially circular, internally-threaded center opening 5, there is a slot-like aperture 17 which extends to the rim 20 of cup 2. Edges 18 and 19 of aperture 17 are rounded and have respective niches 21, 22 at the ends thereof adjacent to rim 20. By means of jaws 23 and 24 of pincers 25, cup 2 can be pressed apart in order to release insert 11 if it becomes necessary to put in a new joint implant. There is no need to remove the old implant partially by means of a chisel as heretofore.

Shown in FIGS. 3 and 4 are a cross-section taken on line III—III of FIG. 2 and a partial elevation in the direction of arrow A thereof, respectively.

Figure 5:
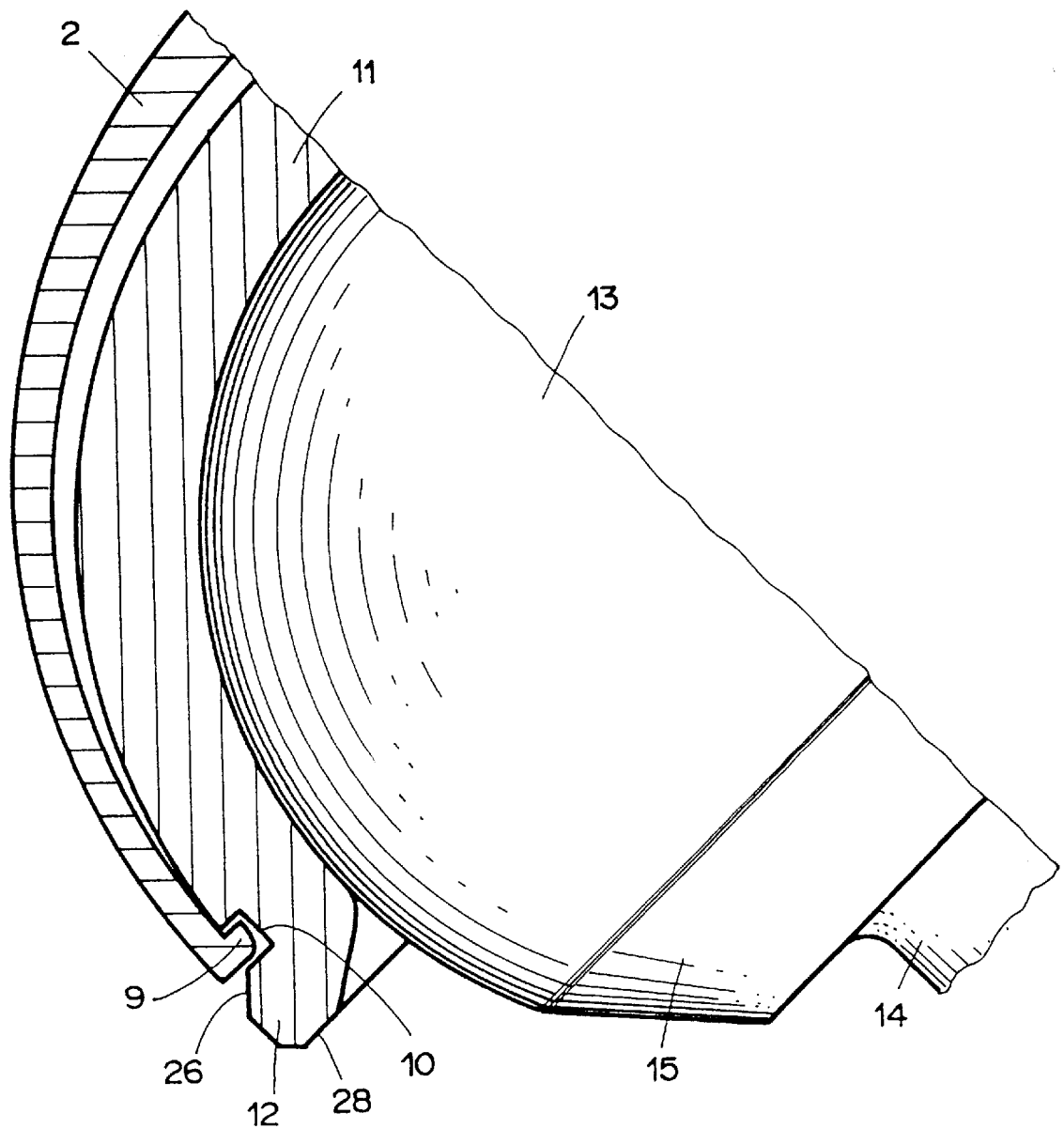
FIG. 5 is a detail of the prosthesis in the first embodiment, analogous to FIG. 1, showing the cup and insert joined.

FIG. 5 shows the area of engagement between cup 2 and insert 11 on a larger scale. The transmission of force takes place from femoral stem 16 via neck 14 to head 13, from the latter to insert 11, and from shoulder 12 of insert 11 to flange 9 of cup 2. Cup 2 does not touch insert 11 elsewhere, so that the introduction of force from the latter to cup 2 takes place optimally at the rim of insert 11. The radii of curvature of cup 2 and of insert 11 are such that these two elements come in contact only at their edges. Thus, cup 2 optimally absorbs the forces exerted by the leg on the femoral stem and distributes them to the acetabulum. Ball head 13 and insert 11 deviate somewhat from the spherical so that the synovia may be well distributed.

Figure 6:
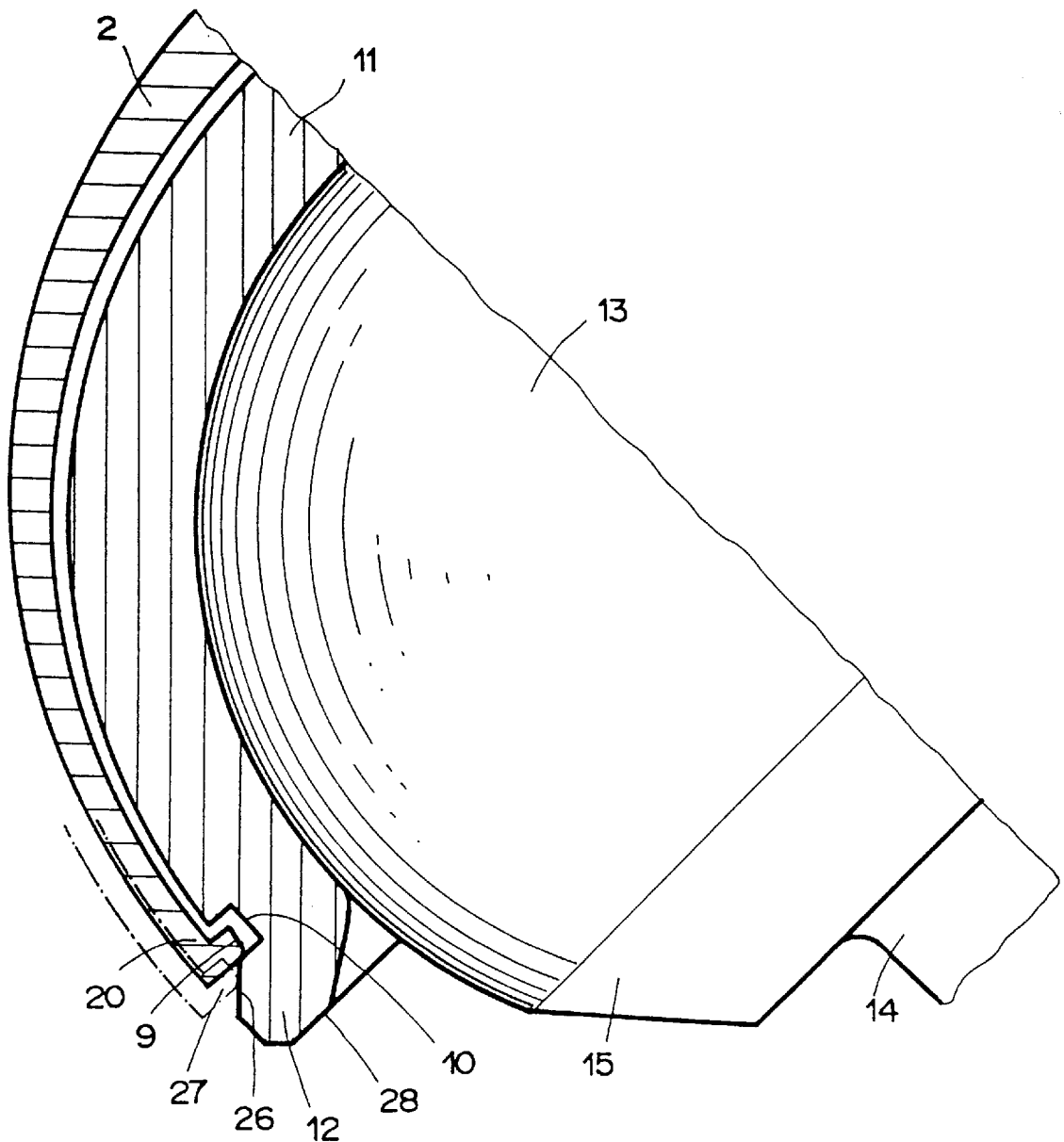
FIG. 6 is another detail, similar to FIG. 5, illustrating the cup and insert in another relative position.

FIG. 6 likewise shows an enlargement of the area where cup 2 engages insert 11. If these components are pressed against one another by a major action of force, flange 9 at the rim of cup 2 can move downward over a surface 26 on shoulder 12 into the position illustrated by dot-dash line 27 without damage to insert 11, i.e., particularly without shoulder 12 breaking off. Surface 26 is preferably inclined at about 45° to edge face 28.

Figure 7:
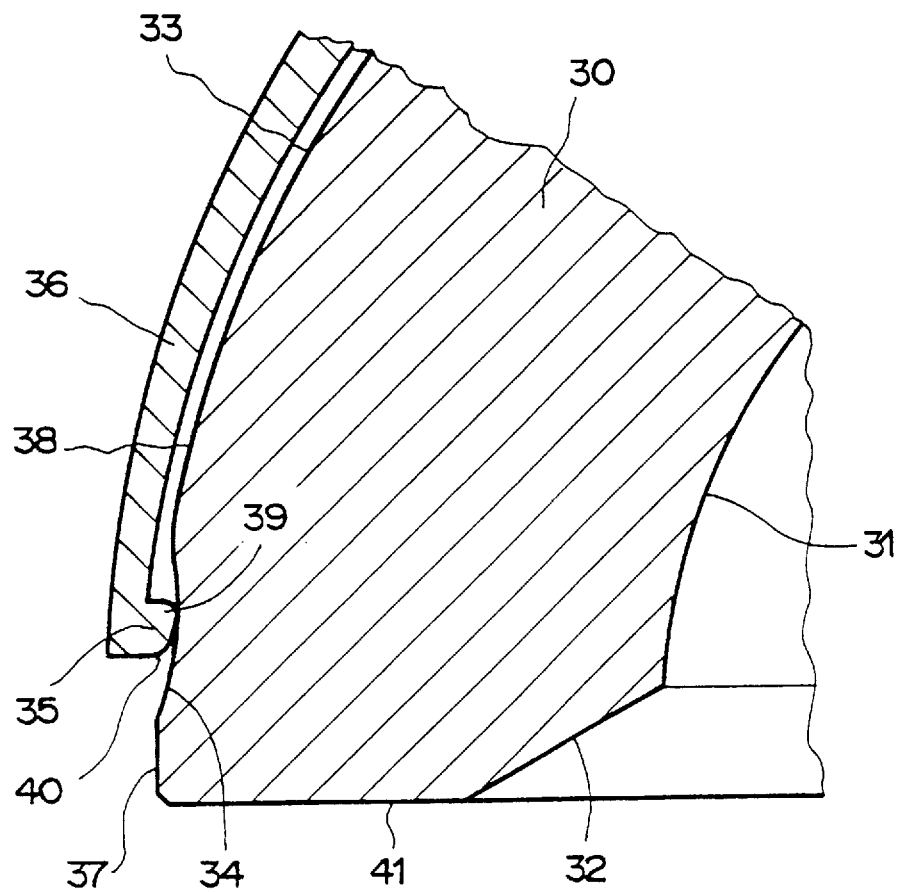
FIG. 7 is a cross-sectional detail of the prosthesis in a second embodiment of the invention.

FIG. 7 is a detail of the prosthesis in a second embodiment of the invention. An insert 30, substantially in the shape of a hollow hemisphere, is thicker than that of the first embodiment in order to increase stability. The ground inside surface 31 of insert 30 serves to receive the femoral ball head (not shown). Adjacent to inside surface 31, insert 30 is provided with a chamfer 32 which merges into an edge face 41. The outside surface 33 of insert 30 has a circular groove 34 near the bottom, as viewed in FIG. 7, which is engaged by a flange 35 of a cup 36. Groove 34 has a flattened U cross-section and is annular. It could, however, have a different cross-section. The transmission of force from the ball head to insert 30 and then to cup 36 takes place as in the first embodiment. From groove 34, the force is transmitted via flange 35 to cup 36, which touches insert 30 only in the region of flange 35. The diameter of insert 30 is somewhat greater in the part designated by reference numeral 37, beneath groove 34 as viewed in FIG. 7, than in the part designated 38 above groove 34. As compared with the first embodiment, the top edge 39 of flange 35 is additionally rounded, the bottom rounding 40 being provided in the first embodiment as well.

Otherwise, the prosthetic joint in the second embodiment of the invention, illustrated in FIG. 7, is designed the same as in the first embodiment.

What is claimed is:

1. A cup, especially for a hip joint prosthesis, having a rim, said cup comprising an aperture having side edges and extending from an interior of said cup to said rim, each of said side edges including at least one niche for the placement of pincers, and said rim including first engagement means running along at least part of said rim for engagement with an insert.

2. The cup of claim 1, wherein said first engagement means are flanges.

3. The cup of claim 2, wherein said first engagement means are at least partially rounded.

4. A cup, especially for a hip joint prosthesis, having a rim, said cup comprising an aperture having side edges and extending from an interior of said cup to said rim, each of said side edges including at least one niche for the placement of pincers, and said rim including first engagement means running along at least part of said rim for engagement with an insert, wherein
said at least one niche is disposed at a transition from said side edges to said rim.

5. The cup of claim 1, wherein said cup has a first side and an opposite side, said opposite side having a greater thickness than said first side.

6. The cup of claim 1 taking the form of a part-spherical hollow element.

7. The cup of claim 1, further comprising an internally threaded bore substantially centrally disposed in said cup, said aperture extending into said bore.

8. The cup of claim 1, made of a titanium-aluminum alloy.

9. A prosthetic joint comprising a cup and an insert, said cup having a rim, an aperture having side edges and extending from an interior of said cup to said rim, each of said side edges including at least one niche for the placement of pincers, and said rim including first engagement means running along at least part of said rim for engagement with said insert, said insert having an edge face and second engagement means running along adjacent to at least part of said edge face for engagement with said cup, said first engagement means of said cup engaging said second engagement means of said insert, said cup and said insert coming in contact only at a point of engagement between said first and second engagement means.

10. The prosthetic joint of claim 9, wherein said first engagement means is a flange and said second engagement means is a groove.

11. A cup, especially for a hip joint prosthesis, having a rim, said cup comprising an aperture having side edges and extending from an interior of said cup to said rim, each of said side edges including at least one niche for the placement of pincers, and said rim including first engagement means running along at least part of said rim for engagement with an insert;
    wherein said first engagement means are flanges;
    wherein said cup has a first side and an opposite side, said opposite side having a greater thickness than said first side; and
    wherein said cup is made of titanium-aluminum alloy.

12. A cup, especially for a hip joint prosthesis, having a rim, said cup comprising an aperture having side edges and extending from an interior of said cup to said rim, each of said side edges including at least one niche for the placement of pincers, and said rim including first engagement means running along at least part of said rim for engagement with an insert;
    wherein said first engagement means are flanges which are at least partially rounded;
    wherein said cup has a first side and an opposite side, said opposite side having a greater thickness than said first side; and
    wherein said cup is made of titanium-aluminum alloy.

* * * * *